US010295517B2

(12) United States Patent
Birks et al.

(10) Patent No.: US 10,295,517 B2
(45) Date of Patent: May 21, 2019

(54) HEATED GRAPHITE SCRUBBER TO REDUCE INTERFERENCES IN OZONE MONITORS

(71) Applicant: Ludlum Measurements, Inc., Sweetwater, TX (US)

(72) Inventors: John W. Birks, Boulder, CO (US); Andrew A. Turnipseed, Boulder, CO (US); Peter C. Andersen, Boulder, CO (US); Craig J. Williford, Boulder, CO (US)

(73) Assignee: LUDLUM MEASUREMENTS, INC., Sweetwater, TX (US)

( * ) Notice: Subject to any disclaimer, the term of this patent is extended or adjusted under 35 U.S.C. 154(b) by 172 days.

(21) Appl. No.: 14/810,311

(22) Filed: Jul. 27, 2015

(65) Prior Publication Data

US 2016/0025696 A1    Jan. 28, 2016

Related U.S. Application Data

(60) Provisional application No. 62/029,876, filed on Jul. 28, 2014.

(51) Int. Cl.
*G01N 33/00* (2006.01)
*B01D 53/66* (2006.01)

(52) U.S. Cl.
CPC .......... *G01N 33/0039* (2013.01); *B01D 53/66* (2013.01); *B01D 2253/102* (2013.01); *Y02A 50/2347* (2018.01); *Y02A 50/247* (2018.01)

(58) Field of Classification Search
CPC .... G01N 33/0039; G01N 21/31; B01D 53/66; B01D 2253/102; Y02A 50/247;
(Continued)

(56) References Cited

U.S. PATENT DOCUMENTS

| 4,820,905 A | * | 4/1989 | Iwata | ............ D01F 9/32 |
| | | | | 219/388 |
| 5,739,038 A | * | 4/1998 | Burrows | ............ G01N 21/31 |
| | | | | 422/199 |

(Continued)

FOREIGN PATENT DOCUMENTS

JP    H07-038936    *    5/1995

OTHER PUBLICATIONS

US Environmental Protection Agency, "Laboratory Study to Explore Potential Interferences t Air Quality Monitors", Dec. 1999.
(Continued)

*Primary Examiner* — Xiuyu Tai
(74) *Attorney, Agent, or Firm* — Polson Intellectual Property Law P.C.; Christopher R. Sylvain; Margaret Polson

(57) ABSTRACT

The present invention provides a means of greatly reducing interferences from mercury vapor, UV-absorbing compounds and water vapor in the measurement of ozone by UV absorbance. A heated graphite scrubber destroys greater than 99% of ozone passing through it while reducing biases from typical atmospheric UV-absorbing interferents by large factors compared to conventional ozone scrubbers. Substitution of a heated graphite scrubber in place of traditional ozone scrubbers such as hopcalite, metal oxides and heated silver scrubbers, results in a more accurate measurement of ozone by reducing the responses to UV-absorbing interferences and water vapor. The heated graphite scrubber also may be used in combination with other ozone sensors, such as electrochemical and HMOS sensors, to provide a reference measurement with ozone selectively removed and thus greatly reduce contributions from interfering species in those measurement devices as well.

20 Claims, 7 Drawing Sheets

(58) Field of Classification Search
CPC ....... Y02A 50/2347; Y10T 436/178459; Y10T 436/186; Y10T 436/182; Y10T 436/184; Y10T 436/175383; Y10T 436/18; Y10T 436/179228; Y10T 436/177692
See application file for complete search history.

(56) References Cited

U.S. PATENT DOCUMENTS 8,128,131 B2   3/2012   Barnett et al.
8,395,776 B2   3/2013   Birks et al.

OTHER PUBLICATIONS

Hudgens, E..E., and T.E. Kleindienst, "A Study of Interferences in Ozone UV and Chemiluminescence Monitors", Measurement of Toxic and Related Air Pollutants, Proceedings of the U.S. EPA/A&WMA International Symposium., 1994. 6 pages.

Kleindienst, Tadeusz E., Hudgens, Edward E., Smith, David F., McElroy, Frank F., and Bufalini, Jopseph J., "Comparison of Chemiluminescence and Ultraviolet Ozone Monitor Responses in th Presence of Humidity and Photochemical Pollutants", Air & Waste, vol. 43, Feb. 1993. 10 pages.

Kleindienst, T.E., and C.D. McIver, "A Study of Interferences in Ambient Ozone Monitirs", Measurement of Toxic and Related Air Pollutants, vol. I, Proceedings of the U.S. EPA/A&WMA International Symposium, Apr. 29-May 1, 1997. 6 pages.

Leston, Al, and Will Ollison, "Estimated Accuracy of Ozone Design Values: Are They Compromised by Method Interferences?", 1993. 20 pages.

Leston, Alan R., Will M. Ollison, Chester W. Spicer, and Jan Satola, "Potential Interference Bias in Ozone Standard Compliance Monitoring", Air & Waste, vol. 55, Oct. 2005. 9 pages.

Li, Ying, Sang-Rin Lee, and Chang-Yu Wu, "UV-Absorption-Based Measurements of Ozone and Mercuty: An Investigation on Their Mutual Interferences", Aerosol and Air Quality Research, vol. 6, No. 4, 2006. 12 pages.

Maddy, Joel A., "A Test That Identifies Ozone Monitirs Prone to Anomalous Behavior While Sampling Hot and Humid Ambient Air", Air & Waste Management Association Annual Meeting, Jun. 14-18, 1998. 22 pages.

Maddy, Joel A., "Evaluating a Heated Metal Scrubber's Effectiveness in Preventing Ozone Monitors' Anomalous Behavior during Hot and Humid Ambient Sampling", 1999. 18 pages.

Meyer, C.P., C.M. Elsworth, and I.E. Galbally, "Water Vapor Interference in the Measurement of Ozone in Ambient Air by Ultraviolet Absorption", Rev. Sci. Instrum. 62 (1), Jan. 1991. 6 pages.

Wilson, Kevin Locke, "Water Vapor Interference in the UV Absorption Measurement of Atmospheric Ozone", PhD thesis, University of Colorado, 2005. 156 pages.

Wilson, Kevin L., and John W. Birks, "Mechanism and Elimination of a Water Vapor Interference in the Measurement of Ozone by UN Absorbvance", Environmental Science & Technology, vol. 40, No. 20, 2006. 7 pages.

Gulbransen et al, "The Oxidation of Graphite at Temperatures of 600° to 1500° C. and at Pressures of 2 to 76 Torr of Oxygen", Journal of the Electrochemical Society, No. 110:6, pp. 476-483 (1963) [8 pages].

Miller et al, "An Experimental Study of the Oxidation of Graphite in High-Temperature Supersonic and Hypersonic Environments", NASA Technical Note D-3444 (1966) [45 pages].

Intezarova et al, "Thermal Decomposition of Ozone", Institute of Chemical Physics, Academy of Sciences of the USSR, pp. 2326-2331 (1967) [English translation of Russian article from Izvestiya Akademii Nauk SSSR, Seriya Khimicheskaya, No. 11, pp. 2440-2446 (1967)] [6 pages].

Razumovskii et al, "Carbon Nanostructure Reactivity: Reactions of Graphite Powders with Ozone", Fullerenes, Nanotubes, and Carbon Nanostructures, No. 15:1, pp. 53-63 (2007) [12 pages].

\* cited by examiner

HEATED GRAPHITE SCRUBBER TO REDUCE INTERFERENCES IN OZONE MONITORS

BACKGROUND

Ozone is a toxic gas produced in photochemical air pollution as a result of a complex sequence of reactions involving oxides of nitrogen, hydrocarbons and sunlight. The Clean Air Act in the U.S. and similar laws in other countries set limits on ozone concentrations in ambient air. Enforcement of compliance with the U.S. National Ambient Air Quality Standard requires continuous monitoring of ozone concentrations at hundreds of locations, especially during summer months. Compliance monitoring currently is done almost exclusively by the method of UV absorbance of the Hg emission line at 254 nm. Low pressure mercury lamps provide an intense, stable and inexpensive source of radiation at a wavelength very near the maximum in the ozone absorption spectrum.

It is well known that ozone monitors based on UV absorbance suffer from interferences from other species that absorb at 254 nm. Volatile organic compounds (VOCs) that interfere are generally aromatic compounds. Some VOCs have a larger response at 254 nm than ozone itself. For example, Kleindienst et al. (1993) reported that the response of 2-methyl-4-nitrophenol is about 40% higher than ozone.

Mercury provides a particularly strong interference because the electronic energy levels of Hg atoms are resonant with the Hg emission line of the low pressure Hg lamp used in ozone monitors. The relative response to Hg as compared to ozone depends on the temperature and pressure of the lamp and on the efficiency with which the instrument's internal ozone scrubber removes mercury, but is usually in the range 100-1000. The U.S. Environmental Protection Agency (EPA, 1999) reported that at a baseline ozone concentration of approximately 75 parts per billion (ppb), the action of 0.04 ppb Hg (300 $ng/m^3$ at room temperature) caused an increase in measured ozone concentration of 12.8% at low humidity (RH=20-30%) and 6.4% at high humidity (RH=70-80%) using a UV photometric ozone monitor. For dry air, Li et al. (2006) found that 1 ppb of mercury gave a response equal to approximately 875 ppb of ozone in the same model of Thermo Electron Corporation photometric ozone monitor used in the EPA study. This mercury interference can be quite large inside buildings where mercury vapor may be present as a result of past mercury spills (broken thermometers, fluorescent light fixtures, electrical switches, etc.), near mining operations and near various industrial facilities.

Another way in which UV-absorbing compounds and mercury interfere in the measurement of ozone using ozone photometers is by adsorption and desorption from the instrument's internal ozone scrubber. These scrubbers are typically composed of manganese dioxide, charcoal, hopcalite, metal oxide screens or heated silver wool. UV-absorbing species will adsorb to and accumulate on the surfaces of the scrubber material. If the temperature of the scrubber increases, or if the humidity changes, these species may be released from the scrubber and enter the gas stream. While removal of a UV-absorbing compound from the sample stream by the scrubber will cause a positive interference, subsequent release of UV-absorbing species from the scrubber will cause a negative interference. Because UV-absorbing compounds and mercury are present at some level in all outdoor and indoor air, this interference may be responsible for much of the baseline drift that occurs in photometric ozone monitors.

Water vapor is known to be a significant interference in the measurement of ozone by UV absorbance (Meyer et al., 1991; Kleindienst et al., 1993; Kleindienst et al., 1997; Leston and Ollison, 1993; Leston et al., 2005; Hudgens et al., 1994; Maddy, 1998; Maddy, 1998; Wilson and Birks, 2006). The cause of this interference has been attributed to a difference in the transmission of light through the UV absorbance cell during measurements of light intensity of sample air while bypassing or passing through an ozone scrubber (Wilson and Birks, 2006). The ozone scrubber alters the concentration of water vapor within the detection cell by either removing or adding water to the air stream, depending on the recent history of exposure to water vapor. It has been shown that the water vapor interference can be eliminated by use of a DewLine™, which consists of a short length of Nafion® tubing (or multiple tubes in parallel) attached to the inlet of the detection cell (Wilson and Birks, 2006). Nafion® has the property of rapidly and selectively transporting water molecules. Matching the humidity levels of ozone-scrubbed and unscrubbed air by passing through a DewLine™ just prior to entering the absorbance cell effectively eliminates the humidity interference in UV absorbance measurements (Wilson and Birks, 2006). However, Nafion® tubes are restrictive to air flow and become contaminated over time when sampling ambient air and are expensive to replace. For these reasons, it would be desirable to solve the humidity interference problem in UV absorbance measurements of ozone without the use of Nafion® tubes.

The use of a gas-phase scrubber was recently introduced as a means of eliminating interferences from both UV-absorbing species and water vapor (Birks et al., 2013). In this approach, the solid-phase scrubber is replaced with a gas phase scrubber such as nitric oxide. The disadvantage of this approach is that a source gas is required, reducing the portability of the instrument. For applications requiring highly portable instruments or where use of a gas scrubber is prohibitive, a solid phase scrubber that effectively destroys ozone (≥99% destruction) but efficiently passes UV-absorbing compounds and water vapor is highly desirable.

BRIEF SUMMARY

The present disclosure provides a means of greatly reducing, typically by at least 50% but often by an order of magnitude or more, the interferences of mercury, UV-absorbing compounds and water vapor in ozone measurements by replacing a prior art internal ozone scrubber of either a single- or dual-beam UV-based ozone monitor with an internal ozone scrubber utilizing heated graphite. A heated graphite scrubber, which passes the sample to be measured over heated graphite, preferably in the form of one or more graphite tubes, largely eliminates the ozone in the sample while efficiently passing most UV-absorbing compounds, leaving them in the sample. The effects of the temperature of the graphite on ozone destruction and reduction of interferences was investigated, and an optimal temperature for operation of a graphite tube scrubber was found to be in the range of 70-110° C. for measurements of ozone in ambient air. At temperatures lower than 70° C., the destruction of ozone was inefficient, while at temperatures higher than 110° C., unacceptably high concentrations of UV-absorbing compounds were released when air passed through the scrubber, probably due to the oxidation of graphite by oxygen in the sample air. Replacement of the ozone scrubbers in commercially available ozone monitors with heated graphite scrubbers would increase the accuracy of ozone measurements by greatly reducing potential interferences.

The heated graphite scrubber could be used in combination with other forms of ozone detection such as electrochemical, including voltametric and amperometric methods, and heated metal oxide semiconductor (HMOS) ozone detectors, to reduce interferences from other species that produce a signal. By alternating between measurements of ozone-scrubbed and unscrubbed air and calculating the difference, as done in UV-absorbance-based ozone monitors, the additive contributions from interferences could be reduced in any type of ozone measurement using the heated graphite scrubber described here.

Here, graphite, an allotrope of carbon, is distinguished from other forms of carbon, such as charcoal, lampblack (soot) and activated carbon, commonly used in air scrubbers for destroying ozone and/or removing other chemical species. Those materials contain graphite, but also have many other impurities that alter their physical and chemical properties and/or have a high concentration of modified surface sites. These materials are often used as chemical scrubbers because of their very high specific surface area (up to 100 $m^2/g$ or more) and their affinity for a wide range of both polar and non polar compounds. Graphite is a natural deposit of metamorphic origin found in the Earth's crust. It also may be produced synthetically by high-temperature treatment of amorphous carbon materials such as calcined petroleum coke and coal tar pitch, both of which are composed of highly graphitizable forms of carbon. Graphite is often crushed and mixed with a clay or synthetic binder to produce products such as pencil lead, welding rods and machinable materials. The graphite referred to herein is either pure graphite as found in nature or synthesized, or graphite containing an inert binder. In particular, glassy carbon and vitreous carbon, which are much less reactive toward ozone, and carbons formed in incomplete combustion processes such as charcoal, lampblack and activated carbon are not considered to be graphite. Ozone scrubbers made of such materials do not have the desirable chemical/physical properties of destroying ozone while passing other potential interferents described by this invention.

One aspect of the present disclosure is the quantitative destruction of ozone on a heated graphite surface.

Another aspect of this invention is substantial transmission of UV-absorbing compounds and mercury through a heated graphite scrubber.

Another aspect of the present disclosure is the use of a heated graphite scrubber as the internal scrubber of a UV-absorbance ozone monitor as a means of reducing interferences from other UV-absorbing species and from water vapor. The method applies to both single- and dual-beam ozone monitors.

Another aspect of the present disclosure is the use of a heat graphic scrubber in an ozone monitor that utilizes a method of detecting ozone other than UV-absorbance.

Another aspect of the present disclosure is the use of a single or multiple graphite tubes in series or in parallel as the ozone scrubber.

Another aspect of the present disclosure is the use of the heated graphite scrubber in any air processing system wherein the reduction of ozone is desired while passing other UV-absorbing species.

The following embodiments and aspects thereof are described and illustrated in conjunction with systems, tools and methods which are meant to be exemplary and illustrative, not limiting in scope. In various embodiments, one or more of the above described problems have been reduced or eliminated, while other embodiments are directed to other improvements.

Disclosed herein is a method for greatly reducing interferences from UV-absorbing species, such as organic and inorganic compounds, mercury vapor and water vapor in the measurement of ozone by using a heated graphite ozone scrubber in place of other solid-phase scrubbers. In one embodiment, the graphite scrubber is in the form of one or more graphite tubes. Graphite tubes have the advantage of providing very high conductance of air, making it possible to use fans in place of air pumps, thereby allowing lower manufacturing cost, less maintenance and quiet operation. Graphite tubes also minimize the surface area where potentially interfering species can react or be adsorbed. In another embodiment, the graphite ozone scrubber is composed of a bed of granular graphite. Granular graphite has the advantage of requiring a small volume of material to obtain a high surface area of ozone destruction and would be useful for replacement of ozone scrubbers in existing ozone monitors. The optimal surface area of the scrubber, whether tubular or granular, depends on the flow rate through the scrubber, a higher flow rate requiring more surface area. The optimal surface area is the minimum surface area required to destroy an acceptable level of ozone (usually >99%), thus allowing as much potentially interfering compound, like UV-absorbing VOCs or mercury, to pass through the scrubber as possible, because species that are not adsorbed or chemically reacted at the scrubber do not interfere in the ozone measurement.

In addition to the exemplary aspects and embodiments described above, further aspects and embodiments will become apparent by reference to the accompanying drawings forming a part of this specification wherein like reference characters designate corresponding parts in the several views.

Before explaining the disclosed embodiment of the present invention in detail, it is to be understood that the invention is not limited in its application to the details of the particular arrangement shown, since the invention is capable of other embodiments. Exemplary embodiments are illustrated in referenced figures. It is intended that the embodiments and figures disclosed herein are to be considered illustrative rather than limiting. Also, the terminology used herein is for the purpose of description and not of limitation.

DETAILED DESCRIPTION

Figure 1:
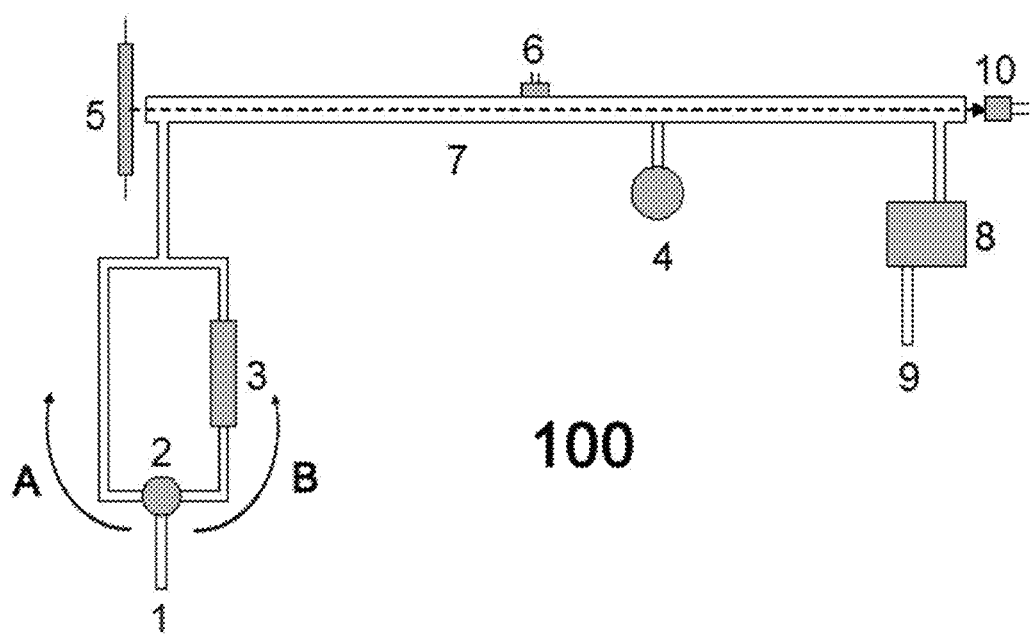
FIG. 1 is a schematic diagram of a single beam ozone monitor based on UV absorbance.

FIG. 1 is a schematic diagram (100) of a single beam ozone monitor based on absorbance of UV light. Other than the ozone scrubber, the ozone monitor is the same as prior art devices and therefore its operating parameters will not be discussed in detail. In general, sample gas such as ambient air is drawn into the instrument through inlet 1 by pump 8. Valve 2 alternately directs the gas sample directly into detection cell 7 (path A) or through an ozone scrubber 3 (path B) and into the detection cell. In a 2B Technologies Model 202 Ozone Monitor, valve 2 switches every two seconds, for example. From the absorbance cell, the sample gas passes through pump 8 and exits the instrument at outlet 9. The sample gas flow rate is typically 0.5 to 3 L/min, with 1 L/min typical for single beam instruments and 2 L/min typical for dual beam instruments. The temperature of the detection cell is measured with temperature sensor 6, and pressure within the detection cell is measured with pressure sensor 4. Lamp 5 produces UV light, which passes through the detection cell and strikes detector 10 to produce a signal proportional to the light intensity. The lamp is normally a low pressure mercury lamp. Detector 10 is normally a phototube or photodiode. A band pass filter centered near 254 nm is commonly placed in front of the detector or built into it in the case of a photodiode to limit detection to the 253.7 nm emission line of mercury. The ozone concentration is calculated, in units of molecules/cm$^3$ for example, using the Beer-Lambert Law, $$[O_3] = \frac{1}{\sigma l}\ln\left(\frac{I_o}{I}\right) \quad (1)$$

where $I_o$ is the detector signal when air is passing through the ozone scrubber (no ozone in detection cell) and I is the detector signal when the sample gas bypasses the ozone scrubber (ozone present in detection cell). Here σ is the absorption cross section for ozone at 253.7 nm ($1.15\times10^{-17}$ cm$^2$/molecule) and/is the length of the detection cell (15 cm for the 2B Technologies Model 202 Ozone Monitor).

The measurements of pressure and temperature allow calculation of the total air molecule concentration within the detection cell using the ideal gas law, so that the concentration of ozone may be expressed as a mixing ratio (mole fraction) in units such as parts-per-billion by volume (ppb).

Note that any species that absorbs light at 253.7 nm will be detected if its concentration is reduced when passing through ozone scrubber 3. However, the values of the light intensity $I_o$ (sample gas passing through scrubber 3) and I (sample gas bypassing scrubber) will be identical if the UV-absorbing species is not removed by the scrubber, and the ozone concentration calculated from equation 1 will be zero. Thus, selectivity against potential interferences from UV-absorbing species other than ozone is achieved if those compounds partially or completely pass through scrubber 3 without being destroyed or removed. The ideal ozone scrubber 3 would destroy or remove all ozone but quantitatively pass all other UV-absorbing compounds. A heated graphite scrubber is a more nearly ideal scrubber than solid-phase ozone scrubbers currently used in ozone monitors.

Figure 2:
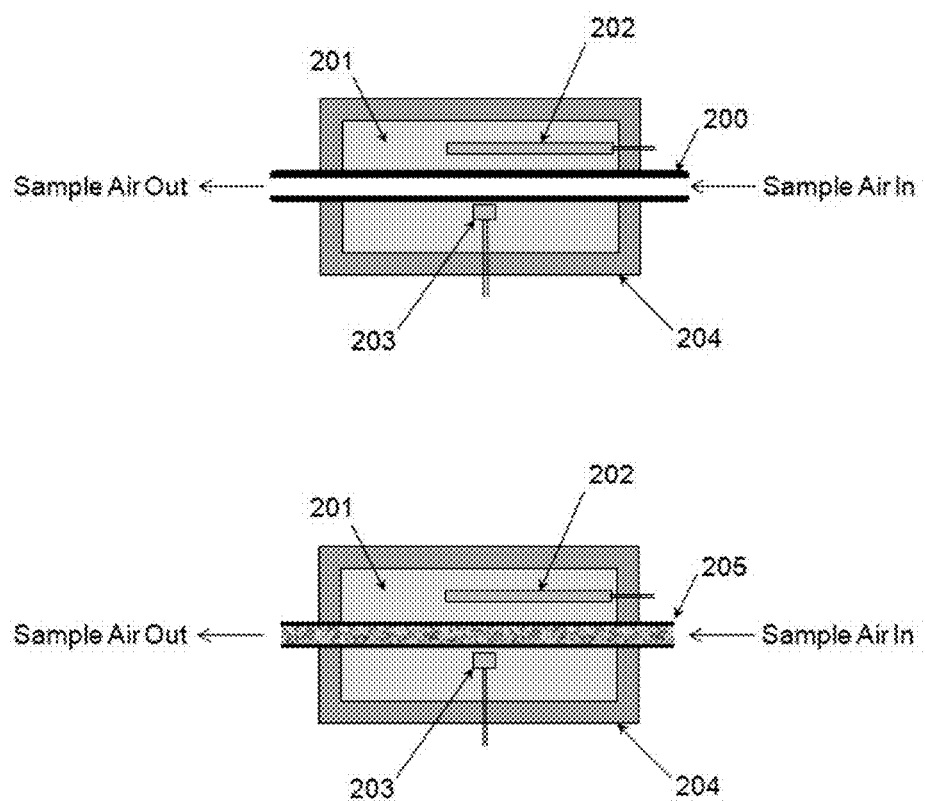
FIG. 2 provides a schematic diagram showing typical heated graphite scrubbers utilizing a heated graphite tube (upper drawing) and a metal or other temperature-resistant tube containing graphite particles (lower drawing).

FIG. 2 is a schematic diagram showing typical heated tubular and packed graphite scrubbers. The upper drawing shows a cross-sectional view along the longitudinal axis of a graphite tube (200) housed in a typical temperature-controlled heating block consisting of a metal (typically aluminum or stainless steel) or ceramic block (201) to provide thermal mass, with cartridge heater (202), temperature sensor (203) and insulation (204). The lower drawing shows a cross-sectional view along the longitudinal axis of a temperature-resistant tube (typically aluminum, stainless steel, alumina, glass, quartz or graphite) packed with graphite particles (205) within the same heating block. This tube could also be an open tube with the interior coated with graphite. Typically a temperature controller monitors the temperature sensor and varies the current through the cartridge heater to maintain a chosen temperature within a narrow range of typically 1° C. or better. Many methods of maintaining a constant elevated temperature of the graphite scrubber are known and can be used with either tubular or packed graphite scrubbers. In particular, a current can be passed directly through the graphite tube so that the graphite tube simultaneously serves as the heating element, as is done in graphite furnace atomic absorption spectroscopy. Note that multiple graphite tubes or multiple tubes packed with graphite particles may be used in parallel in order to enhance the flow conductance of the scrubber. In that case, the multiple tubes may be inserted into the same heating block (201). Individual tubular or packed graphite scrubbers may be used in series to increase the surface area to which ozone is exposed, but at the cost of reduced conductance.

Figure 3:
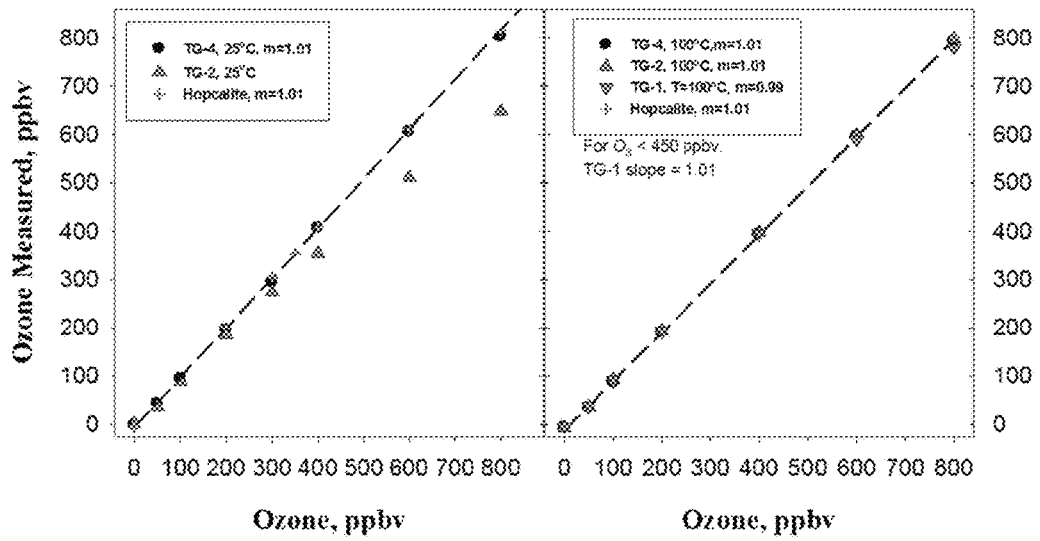
FIG. 3 shows the results of measurements of ozone using a 2B Technologies Model 202 ozone monitor with its standard hopcalite ozone scrubber and with different graphite scrubbers installed in place of the hopcalite scrubber.

FIG. 3 compares the abilities of different ozone scrubbers to destroy ozone. Experiments were performed with a 2B Technologies Model 202 Ozone Monitor with its normal hopcalite scrubber installed and with TG-1, TG-2 and TG-4 scrubbers installed at temperatures of 25° C. and 100° C. TG-1 is a single graphite tube 6 inches in length, TG-2 consists of two 6-inch long graphite tubes in parallel, and TG-4 consists of four 6-inch graphite tubes in parallel. The graphite tubes were obtained from Ohio Carbon Blank, Inc. (EDM-AF5) and are ¼-in o.d. and ⅛-in i.d. Graphite tubes are widely used in the tooling, mold making and general manufacturing industries. The ozone monitor was exposed to known concentrations of ozone in the range 0-800 ppb. The hopcalite scrubber is known to destroy >99% of the ozone and serves as a control. Rounding to three significant figures, the slopes of the linear regressions using the hopcalite scrubber are 1.01 at 25° C. A slope of 1.00 is expected if the instrument and ozone source are both perfectly calibrated. At 25° C., the TG-4 scrubber provides a regression slope of 1.01 as well, showing that it provides the same degree of ozone scrubbing (>99%) as the traditional hopcalite scrubber. The TG-2 scrubber, however, provides a downwardly curved plot at 25° C., indicating that it is not an adequate ozone scrubber at room temperature. At 100° C., hopcalite, TG-2 and TG-4 scrubbers all provide regression slopes of 1.01, indicating that TG-2 and TG-4 scrubbers both destroy ~100% of the ozone. At 100° C., the TG-1 scrubber provides a slope of 0.987 over the range 0-800 ppb and a slope of 1.01 over the range 0-400 ppb, showing that a single graphite tube is an adequate scrubber for ozone concentrations up to 400 ppb but not up to 800 ppb. These results are consistent with the expectation that ozone destruction is more effective at higher temperatures and for higher surface areas and longer residence times of exposure.

Figure 4:
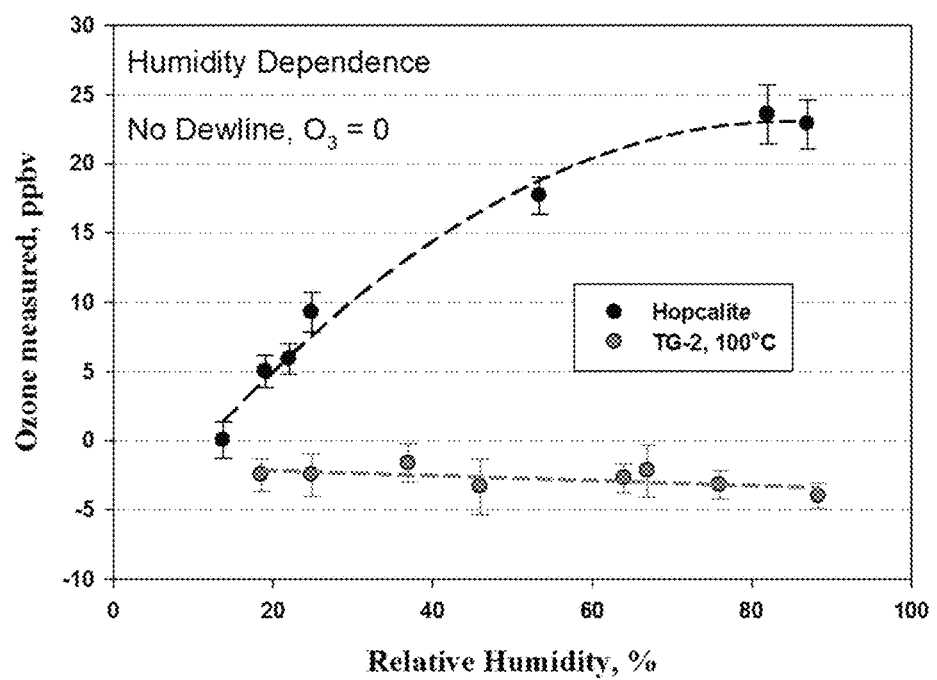
FIG. 4 shows the responses to changes to relative humidity of a 2B Technologies Model 202 ozone monitor response with the DewLine™ removed using the standard unheated hopcalite ozone scrubber and a TG-2 (two 6-inch long graphite tubes in parallel) ozone scrubber.

FIG. 4 shows the effect of varying the relative humidity of air passing through a 2B Technologies Model 202 Ozone Monitor with its internal DewLine™ (Nafion®) tube) removed and using either the standard hopcalite or a TG-2 ozone scrubber. With the DewLine™ removed, there is a >20 ppb increase in the offset of the ozone measurement as relative humidity is increased from 15-90% using the standard hopcalite scrubber. However, when the hopcalite scrubber is replaced with a TG-2 scrubber at 100° C., the effect of humidity on the offset is seen from FIG. 3 to be very small, with only a ~2 ppb decrease while varying relative humidity over the range 18-90%. The same very small effect of water vapor also was seen when 100 ppb of ozone was present. This experiment demonstrates that the DewLine™ can be eliminated if the standard hopcalite scrubber is replaced with a heated graphite TG-2 scrubber. However, the DewLine™ can be used in combination with the heated graphite scrubber as further assurance that any humidity interference is removed.

Figure 5:
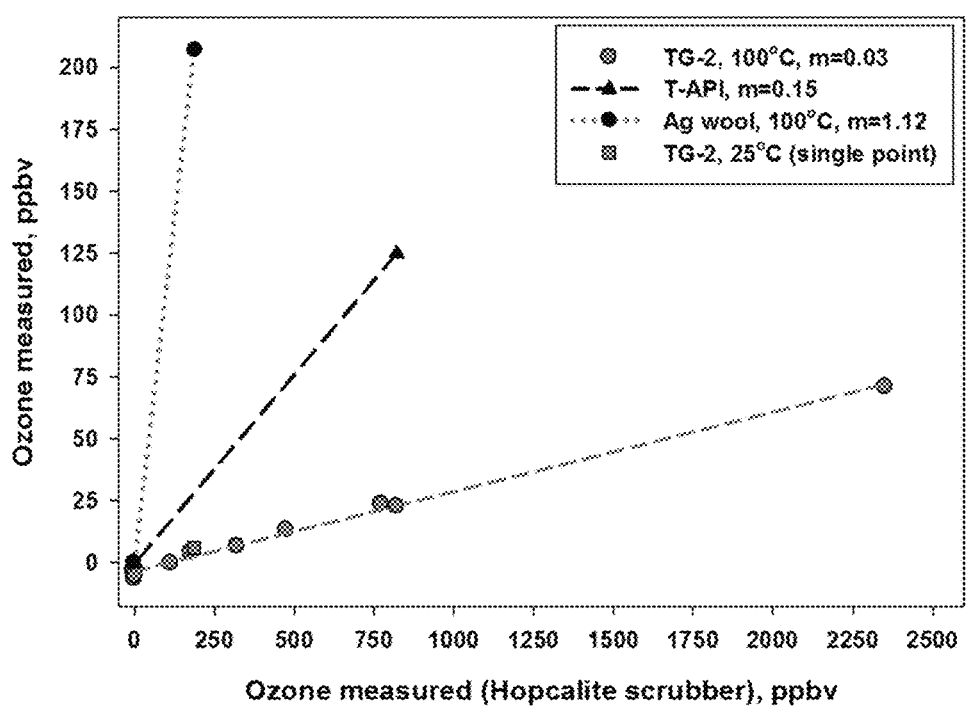
FIG. 5 shows the relative responses of a 2B Technologies Model 202 ozone monitor to mercury vapor with different internal ozone scrubbers.

FIG. 5 is a plot of the relative responses to a source of mercury vapor using different internal scrubbers in a 2B Technologies Model 205 Dual Beam Ozone Monitor. A diffusion source of mercury was used and mercury concentration varied by changing the bath temperature (13 to 160° C.) of the mercury reservoir. Measured equivalent ozone values are plotted for different internal ozone scrubbers vs values obtained using a standard hopcalite scrubber. A TG-2 scrubber at 100° C. gave the smallest response (least interference) of all the scrubbers tested, which also included internal scrubbers taken from a Teledyne-API Model 400E (T-API) ozone monitor and silver wool (Ag wool) scrubber heated to 100° C. (similar to the ozone scrubber used in Horiba Model 360 ozone monitors). Silver wool provides the largest interference, removing ~100% of the mercury vapor, followed by hopalite which removes ~93%. The heated TG-2 scrubber was found to make the ozone monitor ~30 times less sensitive to Hg than the convention hopcalite scrubber.

Figure 6:
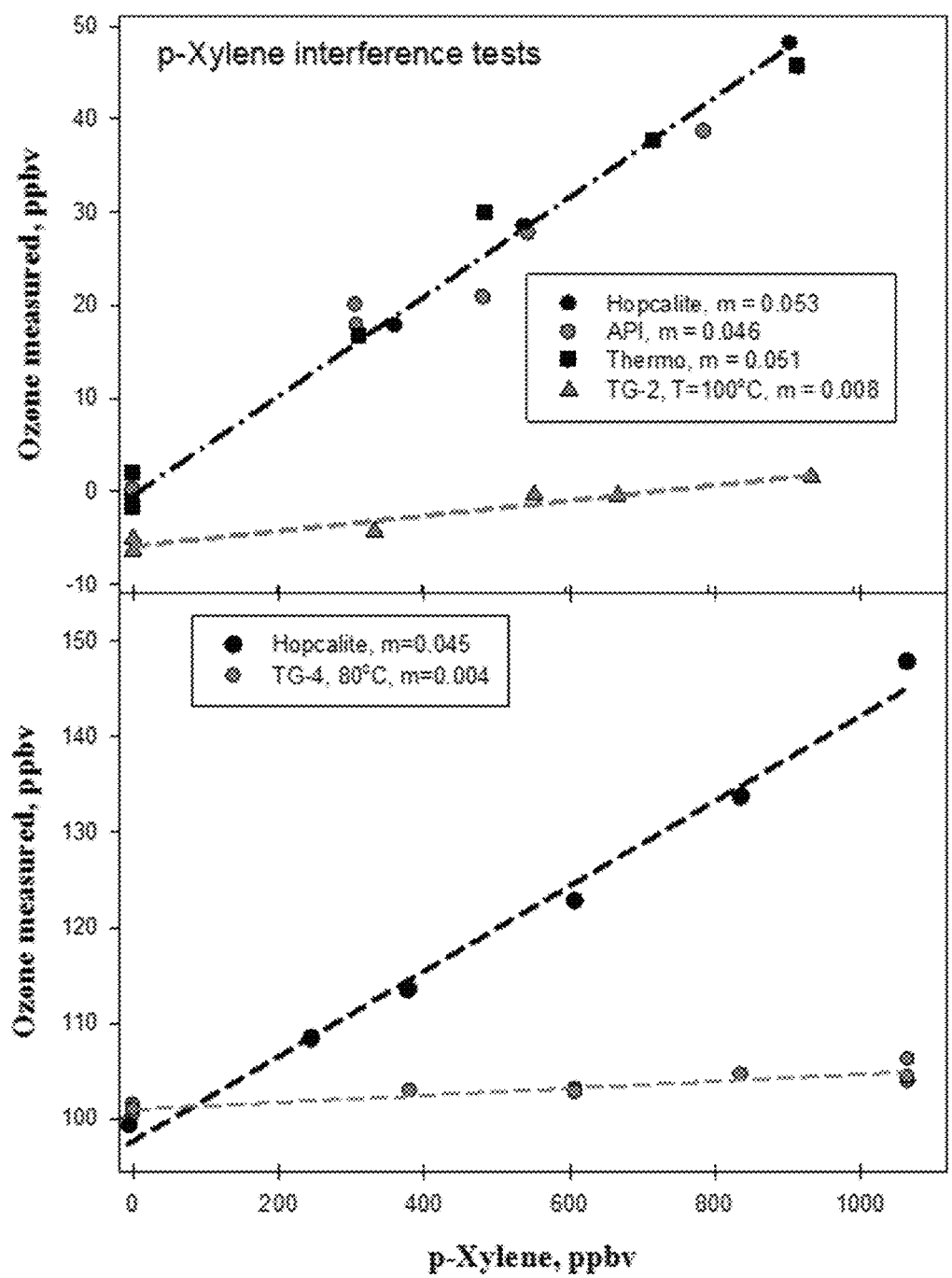
FIG. 6 shows the responses of a 2B Technologies Model 202 ozone monitor to p-xylene using different internal ozone scrubbers.

FIG. 6 shows the response of a 2B Technologies Model 202 ozone monitor fitted with different internal ozone scrubbers to measure concentrations of the common UV-absorbing atmospheric interferent p-xylene. Ozone monitors with hopcalite, Teledyne-API and Thermo scrubbers responded identically within error to p-xylene in dry air. The linear regression slope of 0.053 to the combined data for these scrubbers indicate that ~19 ppb of p-xylene will provide a false signal equivalent to 1 ppb of ozone. The linear regression to the heated TG-2 scrubber yields a slope of 0.008, indicating that it requires ~125 ppb of p-xylene to provide a response equivalent to 1 ppb of ozone, an improvement of a factor of 6.5 over those commercially available scrubbers.

Figure 7:
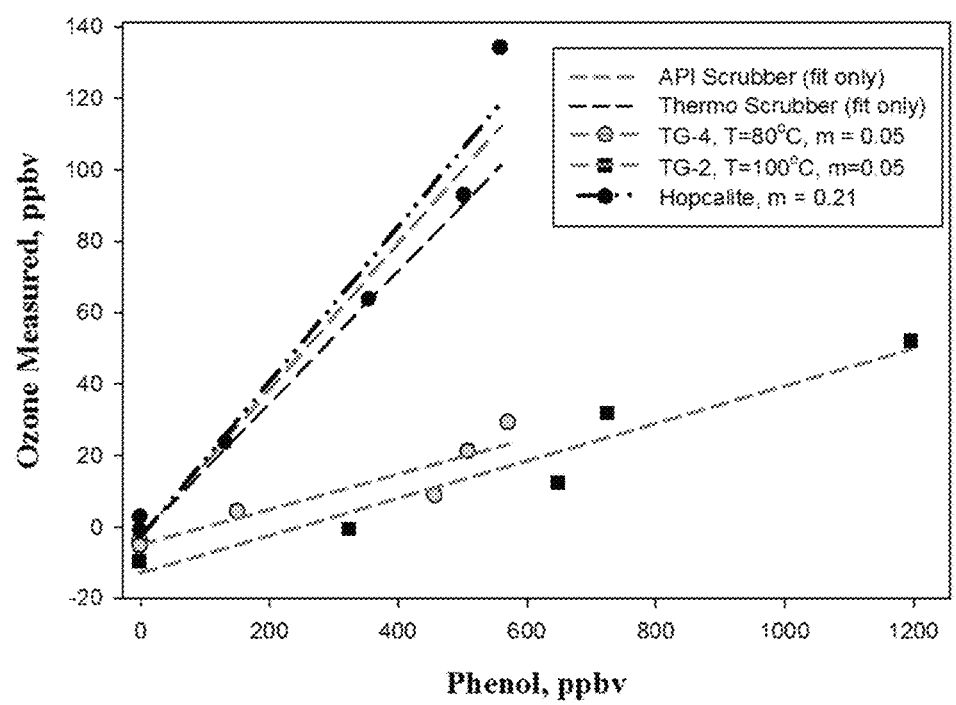
FIG. 7 shows the responses of a 2B Technologies Model 202 ozone monitor to phenol using different internal ozone scrubbers.

FIG. 7 shows the response of a 2B Technologies Model 202 ozone monitor fitted with different internal ozone scrubbers to known concentrations of the common UV-absorbing indoor air interferent phenol. The TG-4 ozone scrubber heated to 80° C. and the TG-2 scrubber heated to 100° C. both gave linear regression slopes of 0.05, meaning that it requires 20 ppb of phenol to provide a response equivalent to 1 ppb of ozone. This is an improvement of a factor of ~4 compared to the T-API, Thermo and hopcalite scrubbers.

CITED LITERATURE

Birks, J. W.; Andersen, P. C.; Williford, C. J. (2006) Ozone monitor with gas phase scrubber, U.S. Pat. No. 8,395,776 B2.

Hudgens, E. E.; Kleindienst, T. E.; McElroy, F. F.; Ollison, W. M. (1994) A study of interferences in ozone UV and chemiluminescent monitors. In *International Symposium on Measurement of Toxics and Related Air Pollutants—Research Triangle Park, N.C.*; Proceedings of Air and Waste Management Association; VIP-39, Air Waste Manage. Assoc.: Pittsburgh, Pa.; pp 405-415.

Kleindienst, T. E.; Hudgens, E. E.; Smith, D. F.; McElroy, F. F.; Bufalini, J. J. (1993) Comparison of chemiluminescence and ultraviolet ozone monitor responses in the presence of humidity and photochemical pollutants. *J. Air Waste Manage. Assoc.* 1993, 43, 213-222.

Kleindienst, T. E.; McIver, C. D.; Ollison, W. M. (1997) A study of interferences in ambient ozone monitors. In *International Symposium on Measurement of Toxics and Related Air Pollutants—Research Triangle Park, N.C.*; Proceedings of Air and Waste Management Association; VIP-74, Air Waste Manage. Assoc.: Pittsburgh, Pa.; pp 215-225.

Leston, A.; Ollison, W. (1993) Estimated accuracy of ozone design values: are they compromised by method interference? In *Tropospheric Ozone: Nonattainment and Design Value Issues—Boston, Mass.*; Proceedings of Air and Waste Management Association; TR-23, Air Waste Manage. Assoc.: Pittsburgh, Pa., 1993; pp 451-456.

Li, Y., Lee, S-R. and Wu, C-Y. (2006) "UV-absorption-based measurements of ozone and mercury: An investigation on their mutual interferences," *Aerosol and Air Quality Research* 6, 418-429.

Leston, A. R.; Ollison, W. M.; Spicer, C. W.; Satola (2005) J. Potential interference bias in ozone standard compliance monitoring. In *Symposium on Air Quality Measurement Methods and Technology*, Proceedings of the AMMA Specialty Conference, VIP-126-CD, Research Triangle Park, N.C., Air Waste Management Assoc.: Pittsburgh, Pa.

Maddy, J. A. (1998) A test that identifies ozone monitors prone to anomalous behavior while sampling hot and humid air. In *Air and Waste Management Association Annual Meeting—San Diego, Calif.*; Proceedings of Air and Waste Management Association; Air Waste Manage. Assoc.: Pittsburgh, Pa.

Maddy, J. A. (1999) Evaluating a heated metal scrubbers effectiveness in preventing ozone monitor's anomalous behavior during hot and humid ambient sampling. In *Air and Waste Management Association Annual Meeting—St. Louis, Mo.*; Proceedings of Air and Waste Management Association; Air Waste Manage. Assoc.: Pittsburgh, Pa.

Meyer, C. P.; Elsworth, C. M.; Galbally, I. E. (1991) Water vapor interference in the measurement of ozone in ambient air by ultraviolet absorption. *Rev. Sci. Instrum.* 62, 223-228.

U.S. Environmental Protection Agency (1999) *Laboratory Study to Explore Potential Interferences to Air Quality Monitors*, EPA-454/C-00-002.

Wilson, K. L. (2005) Water vapor interference in the UV absorption measurement of ozone, Ph.D. Thesis, University of Colorado, Boulder, Colo.

Wilson, K. L.; Birks, J. W (2006) Mechanism and elimination of a water vapor interference in the measurement of ozone by UV absorbance, *Environmental Science and Technology* 40, 6361-6367.

The invention claimed is:

1. An ozone scrubber for reducing interferences from water vapor, mercury and UV-absorbing compounds in the measurement of ozone in a sample gas, the ozone scrubber comprising:

at least one graphite tube forming a chamber, the at least one graphite tube being at least a majority graphite by composition;

the chamber adapted to allow the sample gas to flow through and contact the graphite of the at least one graphite tube before exiting;

the at least one graphite tube surrounded by a heating block;

the heating block in thermal communication with a heater;

the heater adapted to maintain the at least one graphite tube at a temperature when the ozone scrubber is functioning;

wherein the temperature is maintained in the range of 70-110° C.;

wherein more than 50% of ozone in the sample gas is scrubbed by the at least one graphite tube when the ozone scrubber is functioning;

wherein at least 50% of water vapor, mercury, p-xylene or phenol in the sample gas passes through the chamber when the ozone scrubber is functioning.

2. The ozone scrubber of claim 1, wherein the at least one graphite tube of the chamber comprises a plurality of graphite tubes plumbed in series or in parallel.

3. The ozone scrubber of claim 1, wherein the temperature is maintained high enough that approximately 99% or more of the ozone in the sample gas is destroyed by the ozone scrubber when the scrubber is functioning.

4. The ozone scrubber of claim 1, wherein the sample gas is flowed through the chamber at a flow rate between 0.5 and 3.0 L/min.

5. The ozone scrubber of claim 1, wherein the ozone scrubber is mounted in a single beam or dual beam ozone monitor which measures UV absorbance of the sample gas.

6. The ozone scrubber of claim 5, wherein the ozone monitor further comprises a sulfonated polytetrafluoroethylene polymer tube arranged downstream from the ozone scrubber.

7. An ozone scrubber for reducing interferences from water vapor, mercury and UV-absorbing compounds in the measurement of ozone in a sample gas, the ozone scrubber comprising:

a chamber adapted to allow the sample gas to flow through the chamber and come into contact with material packed inside the chamber before exiting the chamber;

the material packed inside the chamber being at least a majority graphite by composition;

a heater adapted to maintain the material packed inside the chamber at a temperature when the ozone scrubber is functioning;

wherein the temperature is maintained in the range of 70–110° C.;

wherein more than 50% of ozone in the sample gas is scrubbed by the material packed inside the chamber when the ozone scrubber is functioning;

wherein at least 50% of water vapor, mercury, p-xylene or phenol in the sample gas passes through the chamber when the ozone scrubber is functioning.

8. The ozone scrubber of claim 7, wherein the chamber is packed with graphite particles.

9. The ozone scrubber of claim 7, wherein the temperature is maintained high enough that approximately 99% or more of the ozone in the sample gas is destroyed by the ozone scrubber when the scrubber is functioning.

10. The ozone scrubber of claim 7, wherein the sample gas is flowed through the chamber at a flow rate between 0.5 and 3.0 L/min.

11. The ozone scrubber of claim 7, wherein the ozone scrubber is mounted in a single beam or dual beam ozone monitor which measures UV absorbance of the sample gas.

12. The ozone scrubber of claim 11, wherein the ozone monitor further comprises a sulfonated polytetrafluoroethylene polymer tube arranged downstream from the ozone scrubber.

13. An ozone scrubber for reducing interferences by water vapor, mercury and UV-absorbing compounds in the measurement of ozone in a sample gas, the ozone scrubber comprising:

a chamber adapted to allow the sample gas to flow through the chamber and come into contact with one or more interior surfaces of the chamber before exiting the chamber;

at least a majority of the one or more interior surfaces of the chamber being at least a majority graphite by composition;

the chamber housed within a heating block;

the heating block in thermal communication with a heater;

the heater adapted to maintain the one or more interior surfaces of the chamber at a temperature when the ozone scrubber is functioning;

wherein the temperature is maintained in the range of 70–110° C.;

wherein more than 50% of ozone in the sample gas is scrubbed by the one or more interior surfaces of the chamber when the ozone scrubber is functioning;

wherein at least 50% of water vapor, mercury, p-xylene or phenol in the sample gas passes through the chamber when the ozone scrubber is functioning.

14. The ozone scrubber of claim 13, wherein the one or more interior surfaces of the chamber are formed by at least one graphite tube.

15. The ozone scrubber of claim 14, wherein the at least one graphite tube of the chamber comprises a plurality of graphite tubes plumbed in series or in parallel.

16. The ozone scrubber of claim 13, wherein the one or more interior surfaces of the chamber are coated in graphite.

17. The ozone scrubber of claim 13, wherein the temperature is maintained high enough that approximately 99% or more of the ozone in the sample gas is destroyed by the ozone scrubber when the scrubber is functioning.

18. The ozone scrubber of claim 13, wherein the sample gas is flowed through the chamber at a flow rate between 0.5 and 3.0 L/min.

19. The ozone scrubber of claim 13, wherein the ozone scrubber is mounted in a single beam or dual beam ozone monitor which measures UV absorbance of the sample gas.

20. The ozone scrubber of claim 19, wherein the ozone monitor further comprises a sulfonated polytetrafluoroethylene polymer tube arranged downstream from the ozone scrubber.

* * * * *